United States Patent
Carbunaru et al.

(10) Patent No.: US 9,561,379 B2
(45) Date of Patent: Feb. 7, 2017

(54) NEUROSTIMULATION SYSTEM WITH DEFAULT MRI-MODE

(71) Applicant: BOSTON SCIENTIFIC NEUROMODULATION CORPORATION, Valencia, CA (US)

(72) Inventors: Rafael Carbunaru, Valley Village, CA (US); Salomo Murtonen, Pasadena, CA (US); Jordi Parramon, Valencia, CA (US); Ross Venook, Millbrae, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/908,764

(22) Filed: Jun. 3, 2013

(65) Prior Publication Data

US 2013/0325085 A1   Dec. 5, 2013

Related U.S. Application Data

(60) Provisional application No. 61/655,938, filed on Jun. 5, 2012.

(51) Int. Cl.
*A61N 1/37* (2006.01)
*A61N 1/372* (2006.01)
*A61N 1/08* (2006.01)

(52) U.S. Cl.
CPC ......... *A61N 1/37211* (2013.01); *A61N 1/3718* (2013.01); *A61N 1/08* (2013.01); *A61N 2001/086* (2013.01)

(58) Field of Classification Search
CPC ................. A61N 1/37; A61N 1/3718
USPC .......................................................... 607/62
See application file for complete search history.

(56) References Cited

U.S. PATENT DOCUMENTS

| | | |
|---|---|---|
| 6,516,227 B1 | 2/2003 | Meadows et al. |
| 6,895,280 B2 | 5/2005 | Meadows et al. |
| 6,993,384 B2 | 1/2006 | Bradley et al. |
| 7,539,538 B2 | 5/2009 | Parramon et al. |
| 7,650,184 B2 | 1/2010 | Walter |

(Continued)

OTHER PUBLICATIONS

PCT International Search Report for PCT/US2013/043916, Applicant: Boston Scientific Neuromodulation Corporation, Form PCT/ISA/210 and 220, dated Sep. 12, 2013 (6pages).

(Continued)

*Primary Examiner* — Joseph Dietrich
(74) *Attorney, Agent, or Firm* — Lowe Graham Jones PLLC; Bruce E. Black

(57) ABSTRACT

A neurostimulation device capable of being placed between a stimulation state and an EMI protection state. The neurostimulation device comprises a plurality of electrical terminals configured for being respectively coupled to a plurality of stimulation electrodes, stimulation output circuitry configured for being selectively activated during the stimulation state to output a plurality of stimulation pulses to the plurality of electrical terminals, electromagnetic protection circuitry configured for being selectively activated during the EMI protection state to prevent at least a portion of the electrical current induced on at least one of the electrical terminals by an electromagnetic field entering the stimulation output circuitry, and a controller configured for automatically defaulting the neurostimulation device to the EMI protection state.

28 Claims, 6 Drawing Sheets

(56) References Cited

U.S. PATENT DOCUMENTS

| | | |
|---|---|---|
| 8,019,439 B2 | 9/2011 | Kuzma et al. |
| 2005/0267546 A1 | 12/2005 | Parramon et al. |
| 2007/0021814 A1 | 1/2007 | Inman et al. |
| 2007/0168004 A1 | 7/2007 | Walter |
| 2007/0168007 A1 | 7/2007 | Kuzma et al. |
| 2007/0173910 A1 | 7/2007 | Armstrong |
| 2009/0149906 A1 | 6/2009 | Ameri et al. |
| 2009/0163980 A1 | 6/2009 | Stevenson |
| 2011/0160807 A1* | 6/2011 | Lyden et al. .................. 607/63 |
| 2011/0270362 A1 | 11/2011 | Goedeke et al. |
| 2012/0109246 A1* | 5/2012 | Seifert et al. .................. 607/27 |

OTHER PUBLICATIONS

PCT Written Opinion of the International Search Authority for PCT/US2013/043916, Applicant: Boston Scientific Neuromodulation Corporation, Form PCT/ISA/237, dated Sep. 12, 2013 (7pages).

U.S. Appl. No. 61/612,241, Neurostimulation System for Preventing Magnetically Induced Current in Electronic Circuitry, Inventor: Kiran Gururaj, et al., filed Mar. 16, 2012.

U.S. Appl. No. 61/733,347, Implantable Medical Device Having Electromagnetic Interference Filter Device to Reduce Pocket Tissue Heating, Inventor: Joseph Bocek, et al., filed Dec. 4, 2012.

\* cited by examiner

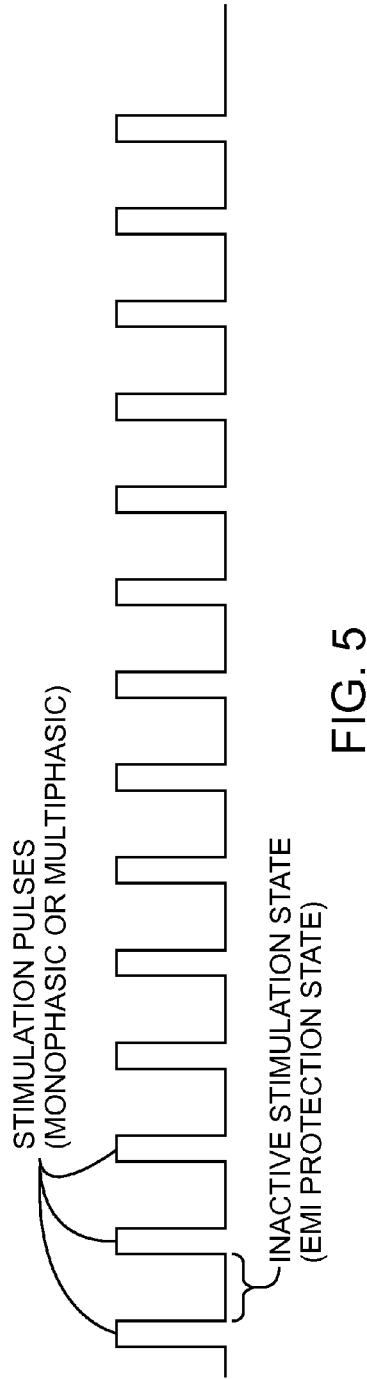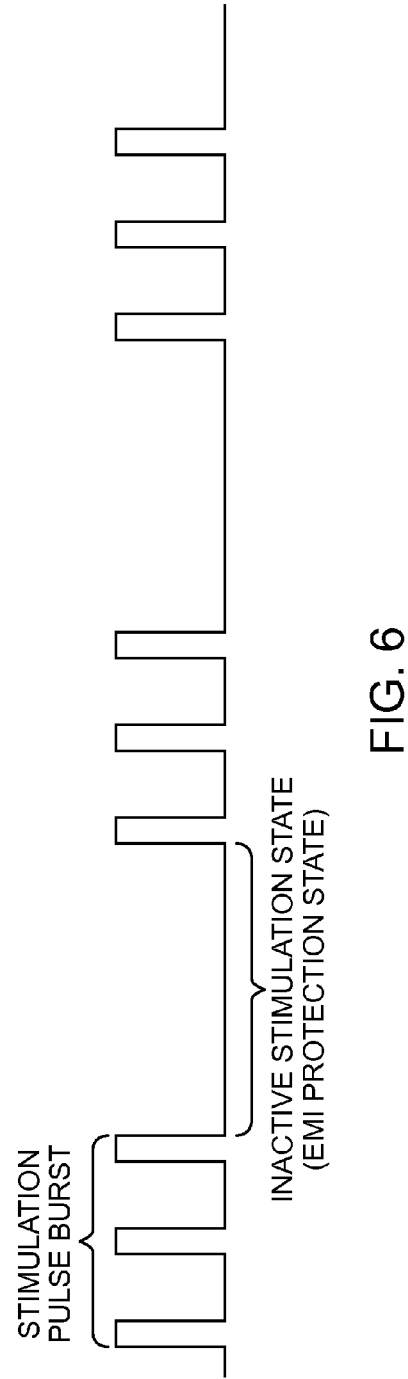

NEUROSTIMULATION SYSTEM WITH DEFAULT MRI-MODE

RELATED APPLICATION DATA

The present application claims the benefit under 35 U.S.C. §119 to U.S. provisional patent application Ser. No. 61/655,938, filed Jun. 5, 2012. The foregoing application is hereby incorporated by reference into the present application in its entirety.

FIELD OF THE INVENTION

The present invention relates to implantable tissue stimulation systems for use in a magnetic resonance imaging (MRI) environment.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes at least one stimulation lead implanted at the desired stimulation site and an Implantable Pulse Generator (IPG) implanted remotely from the stimulation site, but coupled either directly to the stimulation lead(s) or indirectly to the stimulation lead(s) via one or more lead extensions. Thus, electrical pulses can be delivered from the neurostimulator to the electrodes carried by the stimulation lead(s) to stimulate or activate a volume of tissue in accordance with a set of stimulation parameters and provide the desired efficacious therapy to the patient. The neurostimulation system may further comprise a handheld Remote Control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon.

Neurostimulation systems, which may not be limited to SCS used to treat chronic pain, are routinely implanted in patients who are in need of Magnetic Resonance Imaging (MRI). Thus, when designing implantable neurostimulation systems, consideration must be given to the possibility that the patient in which a neurostimulator is implanted may be subjected to electro-magnetic energy from MRI scanners, which may potentially cause damage to patient tissue, malfunction or damage or the neurostimulator, and/or discomfort to the patient.

In particular, in MRI, spatial encoding relies on successively applying magnetic field gradients. The magnetic field strength is a function of position and time with the application of gradient fields throughout the imaging process. Gradient fields typically switch gradient coils (or magnets) ON and OFF thousands of times in the acquisition of a single image in the presence of a large static magnetic field. Present-day MRI scanners can have maximum gradient strengths of 100 mT/m and much faster switching times (slew rates) at or exceeding 200 mT/m/ms, which is capable of generating unintended peripheral nerve stimulation in patients even without the presence of an implantable device. Typical MRI scanners create gradient fields in the range of 1 Hz to 10 KHz, and radio frequency (RF) fields of 64 MHz for a 1.5 Tesla scanner and 128 MHz for a 3 Tesla scanner. Both of these types of applied fields are activated in bursts, which have comparable frequencies to stimulation therapy frequencies.

Because the stimulation leads can act as antennas that collect RF energy, the strength of the RF field generated by a conventional MRI scanner may be high enough to induce voltages on to the stimulation lead(s), which in turn, are seen by the IPG electronics, where it can affect the behavior of the IPG and even result in permanent damage. The RF energy induced in the electrodes may not be distributed homogenously, creating certain areas of higher energy concentration. Even if the total RF energy induced on the stimulation leads could be tolerated by the IPG, undesirable high energy pulses or resulting hot spots may impact IPG performance.

The strength of the gradient magnetic field generated by a conventional MRI scanner can also induce voltage on the stimulation leads, which if higher than the voltage supply rails of the IPG electronics, could cause unwanted stimulation to the patient due to the similar frequency band, between the MRI-generated gradient field and intended stimulation energy frequencies for therapy, as well as potentially damaging the electronics within the IPG. In particular, the gradient magnetic field may induce electrical energy within the wires of the stimulation lead(s), which may be conveyed into the circuitry of the IPG and then out to the electrodes of the stimulation leads via the passive charge recovery switches. For example, in a conventional neurostimulation system, an induced voltage at the connector of the IPG that is higher than IPG battery voltage (typically ~3-5V), may induce such unwanted stimulation currents.

While IPGs can be programmed to switch to a dedicated "MRI mode" that prevents, or at least minimizes, the potentially harmful effects caused by the combination of static, gradient, and RF electromagnetic fields generated by conventional MRIs, known implementations require the neurostimulation system to switch to the dedicated MRI mode prior to or during exposure from the MRI scanner. Therefore, there is a chance that the IPG may not be in the appropriate mode if the IPG resets, if the IPG experiences a failure, if there is failure to detect the occurrence of an MRI, or if there is failure to instruct the IPG to be placed in the MRI mode.

There, thus, remains a need to ensure that an IPG is in an appropriate mode during an MRI.

SUMMARY OF THE INVENTION

In accordance with one aspect of the present inventions, a neurostimulation device capable of being placed between a stimulation state and an electromagnetic interference (EMI) protection state is provided. The neurostimulation device comprises a plurality of electrical terminals configured for being respectively coupled to a plurality of stimulation electrodes. The neurostimulation device further comprises stimulation output circuitry configured for being selectively activated during the stimulation state to output a plurality of stimulation pulses to the plurality of electrical terminals.

The neurostimulation device further comprises electromagnetic protection circuitry configured for being selectively activated during the EMI protection state to prevent at least a portion (and preferably all) of the electrical current induced on at least one of the electrical terminals by an electromagnetic field from entering the stimulation output circuitry (e.g., from entering stimulation sources within the stimulation output circuitry). The electromagnetic protection circuitry, when activated, may optionally be configured for preventing at least a portion of the induced electrical current from being conveyed from the terminal(s) to at least one other of the electrical terminals.

In one embodiment, the electromagnetic protection circuitry, when activated, is configured for preventing at least a portion of the induced electrical current from entering the stimulation output circuitry by applying a high compliance voltage between the electrical terminal(s) and a ground reference. In another embodiment, the electromagnetic protection circuitry, when activated, is configured for preventing at least a portion of the induced electrical current from entering the stimulation output circuitry by introducing a high impedance between the electrical terminal(s) and the stimulation output circuitry. In still another embodiment, the electromagnetic protection circuitry, when activated, is configured for preventing at least a portion of the induced electrical current from entering the stimulation output circuitry by introducing a low impedance between the at least one electrical terminal and a ground reference. In yet another embodiment, the neurostimulation device further comprises a power supply configured for providing power to the stimulation output circuitry, in which case, the electromagnetic protection circuitry, when activated, may be configured for preventing the power from being supplied by the power supply to the stimulation output circuitry.

The neurostimulation device further comprises a controller configured for automatically defaulting the neurostimulation device to the EMI protection state. In one embodiment, the controller is configured for automatically defaulting the neurostimulation device to the EMI protection state in response to a non-user initiated event. The non-user initiated event may be, e.g., one or more of a reset of the neurostimulation device, a fault in the neurostimulation device, a drop in a power supply output below a predetermined level, and a termination of a system test. Or, the non-user initiated event may be the termination of each of the stimulation pulses or the termination of a predetermined burst of stimulation pulses. In another embodiment, the controller is configured for automatically defaulting the neurostimulation device to the EMI protection state in response to a user command to terminate the plurality of stimulation pulses.

In accordance with a second aspect of the present inventions, a method of switching a neurostimulation device (which may be implanted within a patient) between a stimulation state and an EMI protection state is provided. The method comprises outputting a plurality of stimulation pulses from stimulation output circuitry of the neurostimulation device to at least one stimulation lead when the neurostimulation device is in the stimulation state, and exposing the at least one stimulation lead with an electromagnetic field (e.g., generated by a Magnetic Resonance Imaging (MRI) device), thereby inducing an electrical current on stimulation lead(s).

The method further comprises defaulting the neurostimulation device to the EMI protection state. In one method, the neurostimulation device is automatically defaulted to the EMI protection state in response to a non-user initiated event. The non-user initiated event may be, e.g., one or more of a reset of the neurostimulation device, a fault in the neurostimulation device, a drop in a power supply output below a predetermined level, and a termination of a system test. Or, the non-user initiated event may be the termination of each of the stimulation pulses or the termination of a predetermined burst of stimulation pulses. In another method, the neurostimulation device is automatically defaulted to the EMI protection state in response to a user command to terminate the plurality of stimulation pulses.

The method further comprises preventing at least a portion (and preferably all) of the induced electrical current from entering the stimulation output circuitry (e.g., from entering stimulation sources within the stimulation output circuitry) during the EMI protection state. At least a portion of the induced electrical current may be prevented from being conveyed from at least one electrode carried by the stimulation lead(s) and at least another electrode carried by the stimulation lead(s).

In one method, at least a portion of the induced electrical current is prevented from entering the stimulation output circuitry by applying a high compliance voltage between the at least one electrode carried by the stimulation lead(s) and a ground reference. In another method, at least a portion of the induced electrical current is prevented from entering the stimulation output circuitry by introducing a high impedance between at least one electrode carried by the stimulation lead(s) and the stimulation output circuitry. In still another method, at least a portion of the induced electrical current is prevented from entering the stimulation output circuitry by introducing a low impedance between at least one electrode carried by the stimulation lead(s) and a ground reference. In yet another method, at least a portion of the induced electrical current is prevented from entering the stimulation output circuitry by preventing power from being supplied by a power supply to the stimulation output circuitry.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 5 is a timing diagram of a train of stimulation pulses generated by the IPG of FIG. 4;

FIG. 6 is a timing diagram of bursted stimulation pulse trains generated by the IPG of FIG. 4.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a multi-lead system such as a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
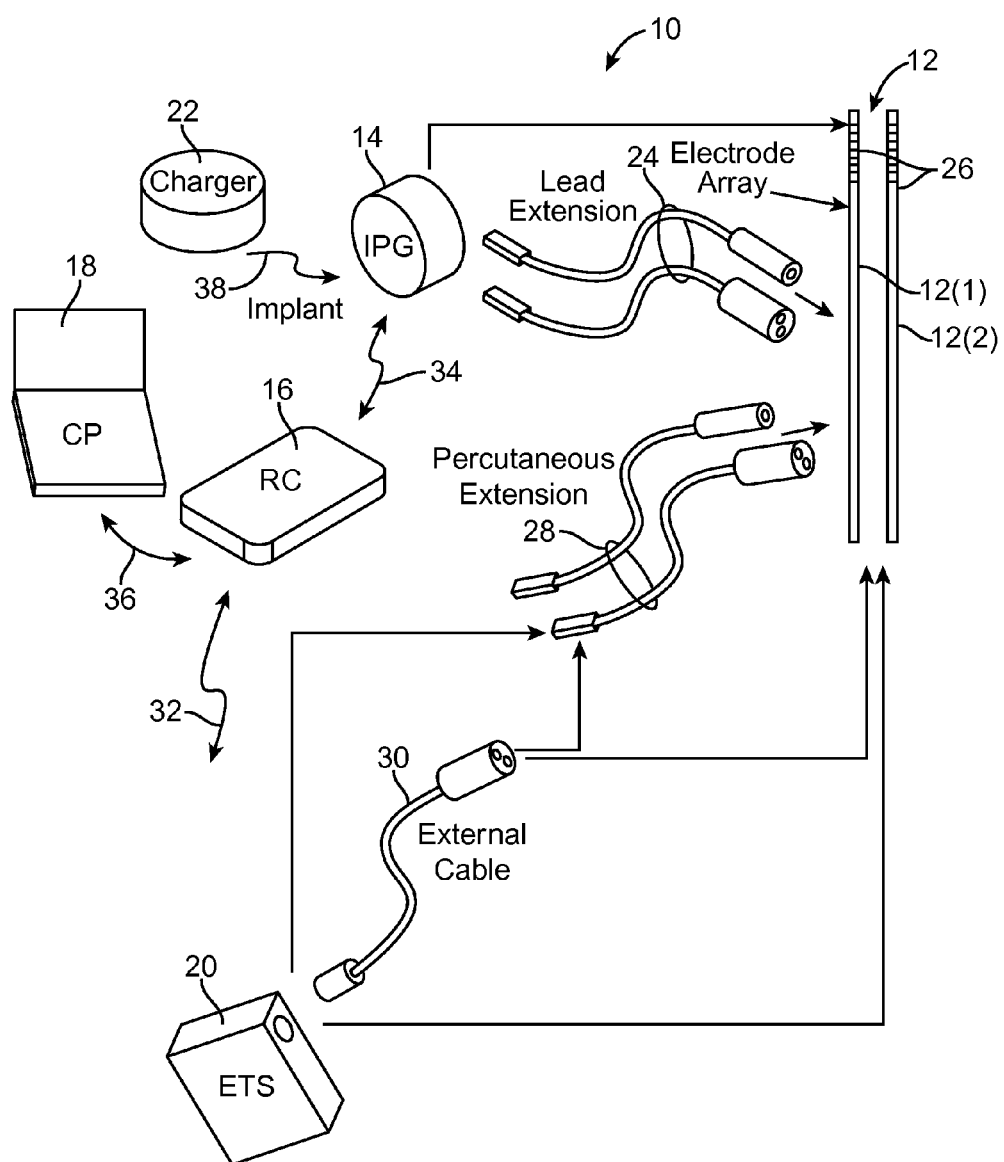
FIG. 1 is plan view of one embodiment of an SCS system arranged in accordance with the present inventions.

Turning first to FIG. 1, an exemplary SCS system 10 generally comprises a plurality of percutaneous stimulation leads 12 (in this case, two percutaneous leads 12(1) and 12(2)), an implantable pulse generator (IPG) 14, an external remote control (RC) 16, a Clinician's Programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. Alternatively, a surgical paddle lead can be used in place of or in addition to the percutaneous leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation lead 12 is implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the CP 18, ETS 20, and external charger 22 will not be described herein. Details of exemplary embodiments of these devices are disclosed in U.S. Pat. No. 6,895,280, which has been previously incorporated herein by reference.

Figure 2:
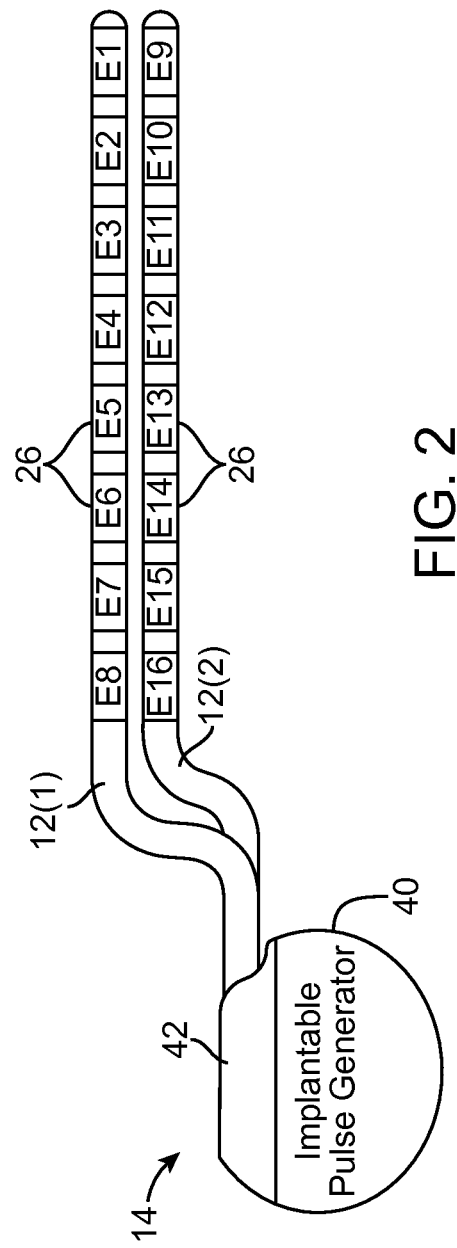
FIG. 2 is a plan view of an implantable pulse generator (IPG) and stimulation leads used in the SCS system of FIG. 1.

Referring now to FIG. 2, the external features of the stimulation leads 12 and the IPG 14 will be briefly described. Each of the stimulation leads 12 has eight electrodes 26 (respectively labeled E1-E8 for the lead 12(1) and E9-E16 for the lead 12(2)). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the stimulation leads 12 mate in a manner that electrically couples the electrodes 26 to the internal electronics (described in further detail below) within the outer case 40. To this end, the connector 42 includes two ports (not shown) for receiving the proximal ends of the three percutaneous leads 12. In the case where the lead extensions 24 are used, the ports may instead receive the proximal ends of such lead extensions 24.

As will be described in further detail below, the IPG 14 includes pulse generation circuitry that provides electrical stimulation energy to the electrodes 26 in accordance with a set of parameters. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 44. Simulation energy may be transmitted to the tissue in a monopolar or multipolar (e.g., bipolar, tripolar, etc.) fashion. Monopolar stimulation occurs when a selected one of the lead electrodes 26 is activated along with the case 44 of the IPG 14, so that stimulation energy is transmitted between the selected electrode 26 and the case 44. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of 15 the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma.

That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse). The recharge pulse may be active, in which case, the electrical current is actively conveyed through the electrode via current or voltage sources, or the recharge pulse may be passive, in which case, the electrical current may be passively conveyed through the electrode via redistribution of the charge flowing from coupling capacitances present in the circuit.

Figure 3:
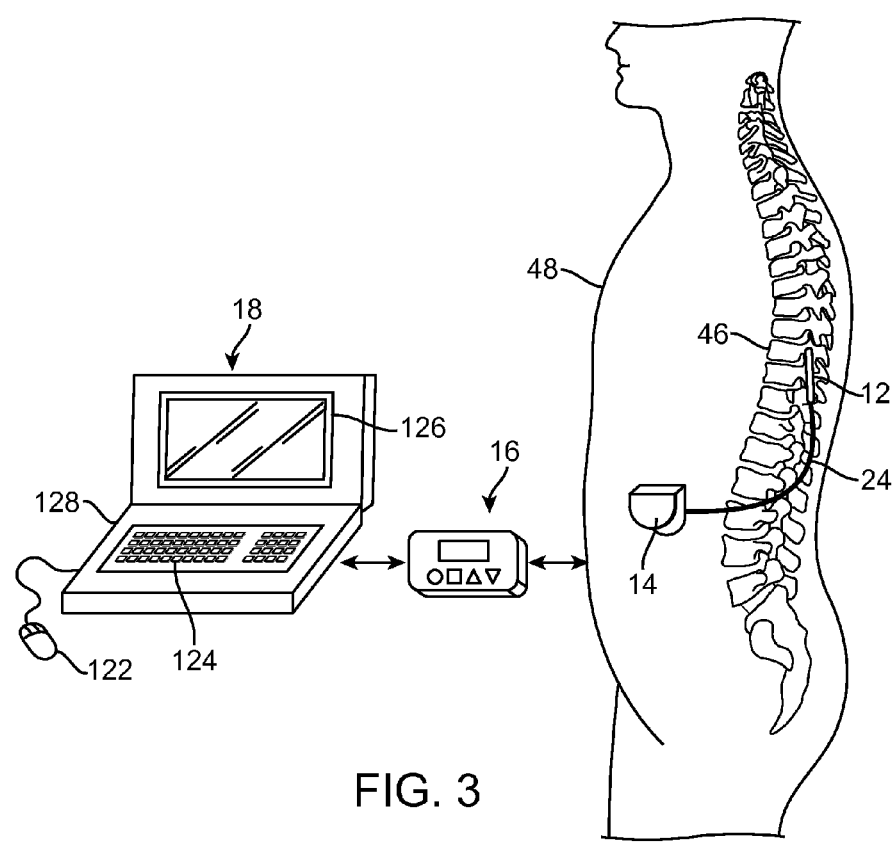
FIG. 3 is a plan view of the SCS system of FIG. 1 in use with a patient.

Referring to FIG. 3, the stimulation leads 12 are implanted within the spinal column 46 of a patient 48. The preferred placement of the stimulation leads 12 is adjacent, i.e., resting near, or upon the dura, adjacent to the spinal cord area to be stimulated. Due to the lack of space near the location where the stimulation leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the stimulation leads 12. As there shown, the CP 18 communicates with the IPG 14 via the RC 16. While the stimulation leads 12 are illustrated as being implanted near the spinal cord area of a patient, the stimulation leads 12 may be implanted anywhere in the patient's body, including a peripheral region, such as a limb, or the brain. After implantation, the IPG 14 is used to provide the therapeutic stimulation under control of the patient.

Figure 4:
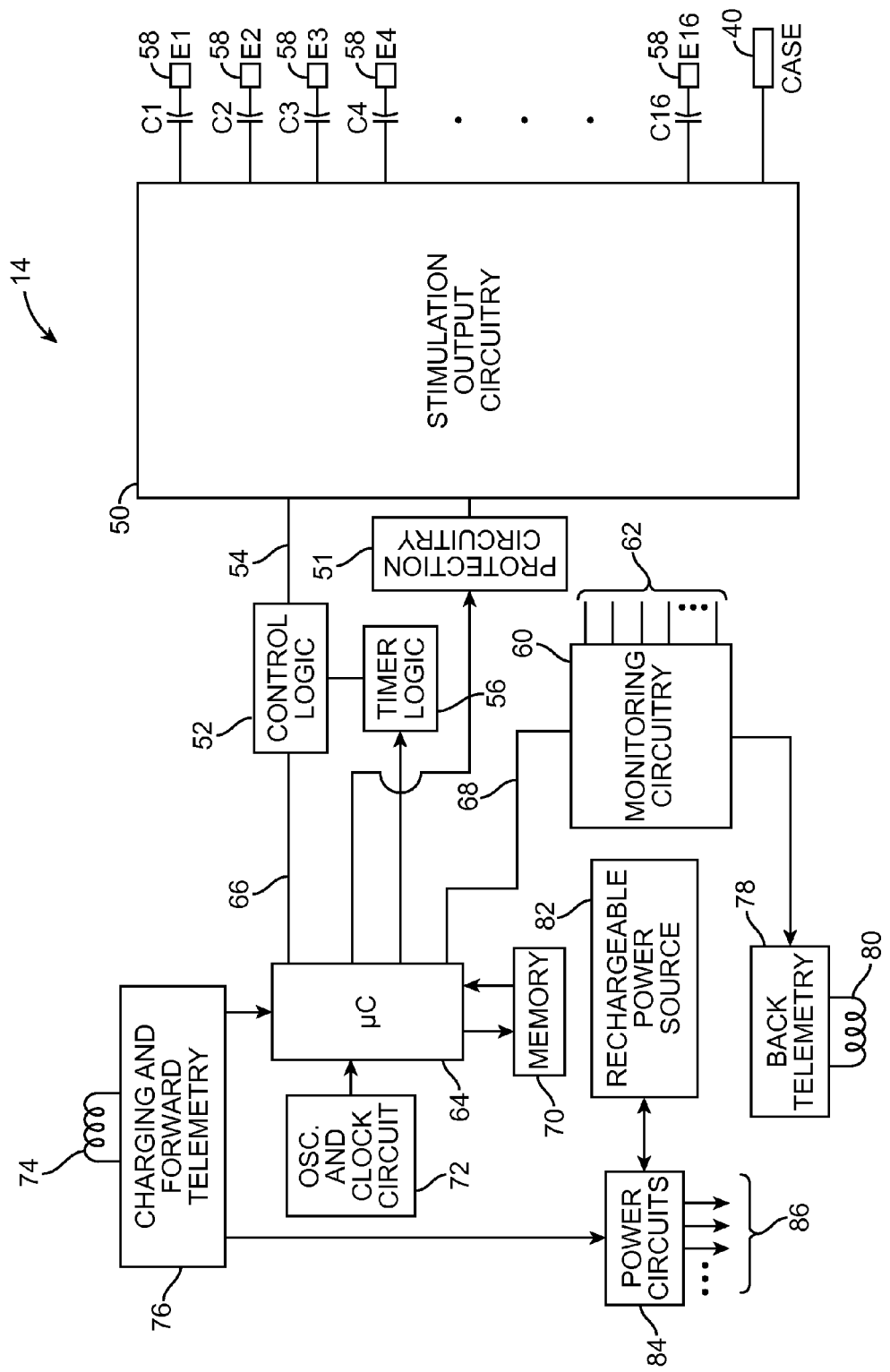
FIG. 4 is a block diagram of the internal components of the IPG of FIG. 1.

Turning next to FIG. 4, the main internal components of the IPG 14 will now be described. The IPG 14 includes stimulation output circuitry 50 configured for generating electrical stimulation energy in accordance with a defined pulsed waveform (a train of stimulation pulses) having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 µs. The stimulation energy generated by the stimulation output circuitry 50 is output via capacitors C1-C16 to electrical terminals 58 corresponding to the electrodes 26.

The stimulation output circuitry 50 may either comprise independently controlled current sources for providing stimulation pulses of a specified and known amperage to or from the electrodes 26, or independently controlled voltage sources for providing stimulation pulses of a specified and known voltage at the electrodes 26. The operation of this stimulation output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 also comprises electrical current induction protection circuitry 51 configured for being selectively activated to prevent at least a portion of electrical current induced on at least one of the electrical terminals 58 by an electromagnetic field (presumably generated by an MRI scanner, but not necessarily limited to an MRI scanner) from entering the stimulation output circuitry 50, and preferably, from entering the stimulation sources included in the stimulation output circuitry 50. For the purposes of this specification, an electromagnetic field may be considered to be a radio frequency (RF) field or a static or time varying magnetic field. In addition to preventing damage to the stimulation output circuitry 50, the protection circuitry 51 is preferably designed to prevent the induced electrical current from being conveyed between the electrical terminals 58 (and thus the electrodes 26) via the stimulation output circuitry 50, so that the patient is not inadvertently stimulated. The protection circuitry 51 is designed, such that the frequency of the induced electrical current, at least a portion of which is prevented from entering the stimulation output circuitry 50, is greater than 500 Hz (e.g., 64 MHz and/or 128 MHz) and less than 1 GHz. The protection circuitry 51 may take the form of any one or combination of various embodiments.

For example, the protection circuitry 51, when activated, may apply a high compliance voltage between the electrical terminals 58 (and thus the electrodes 26) and a ground reference, such as the case 40. In this manner, as long as the electrical current induced on the electrical terminals 58 has a voltage level less than the sum of the high compliance voltage and the threshold voltages of any transistors along the path within the stimulation output circuitry 50, the induced electrical current will be prevented from entering the stimulation output circuitry 50. The protection circuitry 51 may be deactivated by decreasing the compliance voltage to a level adequate for ideal operation during stimulation. Further details discussing the use of high compliance voltages to prevent induced electrical current from entering stimulation output circuitry are set forth in U.S. Provisional Patent Application Ser. No. 61/612,241, entitled "Neurostimulation System for Preventing Magnetically Induced Currents in Electronic Circuitry," which is expressly incorporated herein by reference.

As another example, the protection circuitry 51, when activated, may add relatively high impedances (at the frequencies of interest for the electromagnetic field) between the electrical terminals 58 and the stimulation output circuitry 50. In this manner, the high impedances will prevent the induced electrical current from entering the stimulation output circuitry 50, or at the least, substantially decrease the induced electrical current entering the stimulation output circuitry 50. Such high impedances can be created using components, such as inductors, resistors, solid state devices, etc. The protection circuitry 51 may be deactivated by closing switches in parallel to the high impedance components; in effect, shorting out the components. Further details discussing the use of high impedances to prevent induced electrical current from entering stimulation output circuitry are set forth in U.S. Provisional Patent Application Ser. No. 61/733,347, entitled "Active Implantable Medical Device with Electromagnetic Interference and Pocket Tissue Heating Rejection," which is expressly incorporated herein by reference.

As still another example, the protection circuitry 51, when activated, may include relatively low impedances (at the frequencies of interest for the electromagnetic field) between the electrical terminals 58 (and thus the electrodes 26) and a ground reference, such as the case 40. In this manner, the low impedances will divert the induced electrical current to the ground reference, and will thus, prevent the induced electrical current from entering the stimulation output circuitry 50, or at the least, substantially decrease the induced electrical current entering the stimulation output circuitry 50. Such low impedances can be created using components, such as wires, small value resistors, solid-state devices, switches, relays, etc. The protection circuitry 51 may be deactivated by opening switches in series with the low impedance components; in effect, removing them from the circuit. Further details discussing the use of low impedances to prevent induced electrical current from entering stimulation output circuitry are set forth in U.S. Provisional Patent Application Ser. No. 61/733,347, entitled "Active Implantable Medical Device with Electromagnetic Interference and Pocket Tissue Heating Rejection," which has previously been incorporated herein by reference.

As yet another example, the protection circuitry 51, when activated, may prevent power from being supplied to a power supply (described below) to the stimulation output circuitry 50. This can be accomplished by adding a high impedance or even an open circuit between the power supply and the stimulation output circuitry 50. In this manner, the stimulation output circuitry 50 will be essentially dead, thereby preventing induced electrical current from entering it. The protection circuitry 51 may be deactivated by closing a switch in response to a magnet or external command, thereby supplying power from the power supply to the stimulation output circuitry 50.

The IPG 14 also comprises monitoring circuitry 60 for monitoring the status of various nodes or other points 62 throughout the IPG 14, e.g., power supply voltages, temperature, battery voltage, and the like. Notably, the electrodes 26 fit snugly within the tissue of the patient, and because the tissue is conductive, electrical parameter measurements can be taken at the electrodes 26. In addition to monitoring electrical parameter data on the lead electrodes 26, the monitoring circuitry 60 may also detect the presence of a large magnetic field (e.g., using a reed switch and/or a Hall-effect sensor) or a radio frequency (RF) noise characteristic of an MRI procedure.

The IPG 14 further comprises processing circuitry in the form of a microcontroller (μC) 64 that controls the control logic 52 over data bus 66, and obtains status data from the monitoring circuitry 60 via data bus 68. The IPG 14 additionally controls the timer logic 56. The IPG 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and stimulation parameters. In controlling the operation of the IPG 14, the microcontroller 64 is able to individually generate stimulus pulses at the electrodes 26 using the stimulation output circuitry 50, in combination with the control logic 52 and timer logic 56, thereby allowing each electrode 26 to be paired or grouped with other electrodes 26, including the monopolar case electrode, to control the polarity, amplitude, rate, pulse width and channel through which the current stimulus pulses are provided.

Significantly, the microcontroller 64 may place the IPG 14 between a stimulation mode, during which a train of stimulation pulses (or trains of stimulation pulses in the case of bursting) is generated and conveyed by the stimulation output circuitry 50, and an inactive mode, during which no train or trains of pulses are generated and conveyed by the stimulation output circuitry 50. When the IPG 14 is in the stimulation mode, the IPG 14 can be considered to be in an active stimulation state during the time period in which a stimulation pulse (whether monophasic or multiphasic) is currently generated and conveyed by the stimulation output circuitry 50, and an inactive stimulation state during the time period in which no stimulation pulse is currently generated and conveyed (i.e., the time period between an adjacent pair of stimulation pulses or a time period between trains of pulses).

Significantly, the microcontroller 64 may automatically default the IPG 14 to an electromagnetic interference (EMI) protection state in response to different events by activating the protection circuitry 51, such that it is virtually ensured that the IPG 14 will be in this state when an MRI is being performed on the patient implanted with the IPG 14. The microcontroller 64 may switch the IPG 14 from the EMI protection state to a normal state in response to a user command (e.g., to place the IPG 14 in a stimulation mode).

The microcontroller 64 may automatically default the IPG 14 to the EMI protection state in response to a non-user initiated event. In one embodiment, the non-user initiated event may be, e.g., a reset of the IPG 14, a fault in the IPG 14, a drop in the output of the power supply below a predetermined level, or a termination of a system test.

In another embodiment, the non-user initiated event is the termination of each of the stimulation pulses conveyed by the stimulation output circuitry 50. For example, as illustrated in FIG. 5, the microcontroller 64 defaults the IPG 14 to the EMI protection state during the stimulation mode, and in particular, during the inactive stimulation state between the stimulation pulses, which may be monophasic or multiphasic. In effect, EMI protection state is temporally coincident with the inactive stimulation state between the stimulation pulses. In still another embodiment, the non-user initiated event is the termination of a predetermined burse of stimulation pulses. For example, as illustrated in FIG. 6, the microcontroller 64 defaults the IPG 14 to the EMI protection state during the stimulation mode, and in particular, during the inactive stimulation state between stimulation pulse bursts. In effect, EMI protection state is temporally coincident with the inactive stimulation state between the stimulation pulse bursts.

In yet another embodiment, the microcontroller 64 defaults the IPG 14 to the EMI protection state in response to a user command (e.g., via the RC 16) to terminate the stimulation pulses. In effect, the EMI protection state is temporarily coincident with the inactive stimulation mode of the IPG 14.

Referring back to FIG. 4, the IPG 14 further comprises an alternating current (AC) receiving coil 74 for receiving programming data (e.g., the operating program, and/or stimulation parameters, and/or a signal for placing the IPG 14 in either the normal-mode or the MRI mode) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data sensed through the monitoring circuitry 60 to the RC 16 and/or CP 18. The back telemetry features of the IPG 14 also allow its status to be checked. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18.

The IPG 14 further comprises a rechargeable power source 82 and power circuits 84 for providing the operating power to the IPG 14. The rechargeable power source 82 may, e.g., comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 7:
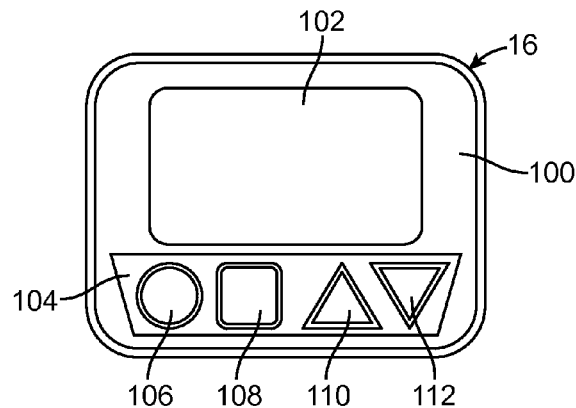
FIG. 7 is front view of a remote control (RC) used in the SCS system of FIG. 1.

Referring now to FIG. 7, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF (in effect, placing the IPG 14 between the stimulation mode and the inactive stimulation mode). The button 108 serves as a select button that allows the RC 106 to switch between screen displays and/or parameters. The buttons 110 and 112 serve as up/down buttons that can be actuated to increase or decrease any of stimulation parameters of the pulse generated by the IPG 14, including pulse amplitude, pulse width, and pulse rate.

Figure 8:
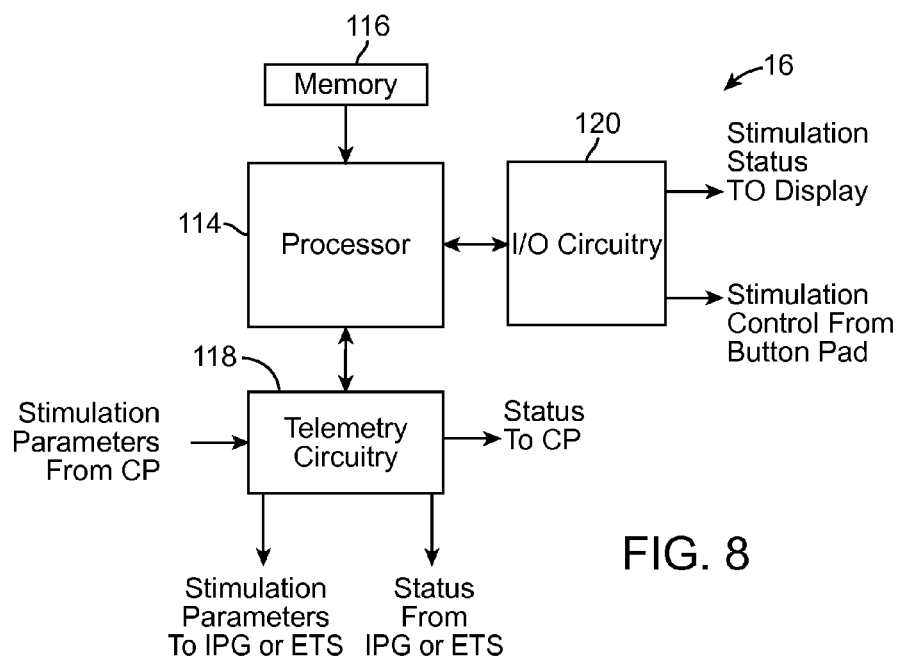
FIG. 8 is a block diagram of the internal components of the RC of FIG. 7.

Referring to FIG. 8, the internal components of an exemplary RC 16 will now be described. The RC 16 generally includes a controller/processor 114 (e.g., a microcontroller), memory 116 that stores an operating program for execution by the controller/processor 114, and telemetry circuitry 118 for transmitting control data (including stimulation parameters, instructions to turn the IPG 14 on or off, and requests to provide status information) to the IPG 14 and receiving status information from the IPG 14 via link 34 (shown in FIG. 1), as well as receiving the control data from the CP 18 and transmitting the status data to the CP 18 via link 36 (shown in FIG. 1). The RC 16 further includes input/output circuitry 120 for receiving stimulation control signals from the button pad 104 and transmitting status information to the display screen 102 (shown in FIG. 7).

Notably, while the controller/processor 114 is shown in FIG. 8 as a single device, the processing functions and controlling functions can be performed by a separate controller and processor. Thus, it can be appreciated that the controlling functions described below as being performed by the RC 16 can be performed by a controller, and the processing functions described below as being performed by the RC 16 can be performed by a processor. Further details of the functionality and internal componentry of the RC 16 are disclosed in U.S. Pat. No. 6,895,280, which has previously been incorporated herein by reference.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation device capable of being placed between a stimulation state and an electromagnetic interference (EMI) protection state, comprising:
   a plurality of electrical terminals configured for being respectively coupled to a plurality of stimulation electrodes;
   stimulation output circuitry configured for being selectively activated during the stimulation state to output a plurality of stimulation pulses to the plurality of electrical terminals;
   electromagnetic protection circuitry configured for being selectively activated during the EMI protection state to prevent at least a portion of an electrical current induced on at least one of the electrical terminals by an electromagnetic field from entering the stimulation output circuitry; and
   a controller configured for automatically defaulting the neurostimulation device from the stimulation state to the EMI protection state in response to a non-user initiated event selected from the group consisting of a drop in a power supply output below a predetermined level and a termination of a system test.

2. The neurostimulation device of claim 1, wherein the electromagnetic protection circuitry, when activated, is configured for preventing the at least a portion of the induced electrical current from entering the stimulation output circuitry by applying a high compliance voltage between the at least one of the electrical terminals and a ground reference.

3. The neurostimulation device of claim 1, wherein the electromagnetic protection circuitry, when activated, is configured for preventing the at least a portion of the induced electrical current from entering the stimulation output circuitry by introducing a high impedance between the at least one of the electrical terminals and the stimulation output circuitry.

4. A neurostimulation device capable of being placed between a stimulation state and an electromagnetic interference (EMI) protection state, comprising:
   a plurality of electrical terminals configured for being respectively coupled to a plurality of stimulation electrodes;
   stimulation output circuitry configured for being selectively activated during the stimulation state to output a plurality of stimulation pulses to the plurality of electrical terminals;
   electromagnetic protection circuitry configured for being selectively activated during the EMI protection state to prevent at least a portion of an electrical current induced on at least one of the electrical terminals by an electromagnetic field from entering the stimulation output circuitry, wherein the electromagnetic protection circuitry, when activated, is configured for preventing the at least a portion of the induced electrical current from entering the stimulation output circuitry by introducing a low impedance between the at least one of the electrical terminals and a ground reference; and
   a controller configured for automatically defaulting the neurostimulation device to the EMI protection state.

5. A neurostimulation device capable of being placed between a stimulation state and an electromagnetic interference (EMI) protection state, comprising:
   a plurality of electrical terminals configured for being respectively coupled to a plurality of stimulation electrodes;
   stimulation output circuitry configured for being selectively activated during the stimulation state to output a plurality of stimulation pulses to the plurality of electrical terminals;
   electromagnetic protection circuitry configured for being selectively activated during the EMI protection state to prevent at least a portion of an electrical current induced on at least one of the electrical terminals by an electromagnetic field from entering the stimulation output circuitry;
   a controller configured for automatically defaulting the neurostimulation device to the EMI protection state; and
   a power supply configured for providing power to the stimulation output circuitry, wherein the electromagnetic protection circuitry, when activated, is configured for preventing the at least a portion of the induced electrical current from entering the stimulation output circuitry by preventing the power from being supplied by the power supply to the stimulation output circuitry.

6. The neurostimulation device of claim 1, wherein the stimulation output circuitry comprises at least one stimulation source, and the electromagnetic protection circuitry, when activated, is configured for preventing the at least a portion of the induced electrical current from entering the at least one stimulation source.

7. The neurostimulation device of claim 1, wherein the electromagnetic protection circuitry, when activated, is configured for preventing the at least a portion of the induced electrical current from being conveyed from the at least one electrical terminal to at least one other of the electrical terminals.

8. The neurostimulation device of claim 1, wherein the electromagnetic protection circuitry, when activated, is configured for preventing all of the induced electrical current from entering the stimulation output circuitry.

9. The neurostimulation device of claim 4, wherein the controller is configured for automatically defaulting the neurostimulation device to the EMI protection state in response to a non-user initiated event.

10. The neurostimulation device of claim 9, wherein the non-user initiated event is one or more of a reset of the neurostimulation device, a fault in the neurostimulation device, a drop in a power supply output below a predetermined level, and a termination of a system test.

11. The neurostimulation device of claim 9, wherein the non-user initiated event is a termination of each of the stimulation pulses.

12. The neurostimulation device of claim 9. wherein the non-user initiated event is a termination of a predetermined burst of stimulation pulses.

13. The neurostimulation device of claim 1, wherein the controller is configured for automatically defaulting the neurostimulation device to the EMI protection state in response to a user command to terminate the plurality of stimulation pulses.

14. A method of switching the neurostimulation device of claim 1 between a stimulation state and an EMI protection state, the method comprising:
   outputting a plurality of stimulation pulses from the stimulation output circuitry of the neurostimulation device to at least one stimulation lead when the neurostimulation device is in the stimulation state;
   exposing the at least one stimulation lead with an electromagnetic field, thereby inducing an electrical current on the at least one stimulation lead;
   defaulting the neurostimulation device to the EMI protection state; and
   preventing at least a portion of the induced electrical current from entering the stimulation output circuitry during the EMI protection state.

15. The method of claim 14, wherein the at least a portion of the induced electrical current is prevented from entering the stimulation output circuitry by applying a high compliance voltage between at least one electrode carried by the at least one stimulation lead and a ground reference.

16. The method of claim 14, wherein the at least a portion of the induced electrical current is prevented from entering the stimulation output circuitry by introducing a high impedance between at least one electrode carried by the at least one stimulation lead and the stimulation output circuitry.

17. The method of claim 14, wherein the at least a portion of the induced electrical current is prevented from entering the stimulation output circuitry by introducing a low impedance between at least one electrode carried by the at least one stimulation lead and a ground reference.

18. The method of claim 14, wherein the at least a portion of the induced electrical current is prevented from entering the stimulation output circuitry by preventing power from being supplied by a power supply to the stimulation output circuitry.

19. The method of claim 14, wherein the stimulation output circuitry comprises at least one stimulation source, and the at least a portion of the induced electrical current is prevented from entering the at least one stimulation source during the EMI protection state.

20. The method of claim 14, wherein the at least a portion of the induced electrical current is prevented from being conveyed from at least one electrode carried by the at least one stimulation lead and at least another electrode carried by the at least one stimulation lead.

21. The method of claim 14, wherein all of the induced electrical current is prevented from entering the stimulation output circuitry during the EMI protection state.

22. The neurostimulation device of claim 5, wherein the neurostimulation device is automatically defaulted to the EMI protection state in response to a non-user initiated event.

23. The neurostimulation device of claim 22, wherein the non-user initiated event is one of a reset of the neurostimulation device, a fault in the neurostimulation device, a drop in a power supply output below a predetermined level, and a termination of a system test.

24. The neurostimulation device of claim 22, wherein the non-user initiated event is a termination of each of the stimulation pulses.

25. The neurostimulation device of claim 22, wherein the non-user initiated event is a termination of a predetermined burst of stimulation pulses.

26. The method of claim 14, wherein the neurostimulation device is automatically defaulted to the EMI protection state in response to a user command to terminate the plurality of stimulation pulses.

27. The method of claim 14, wherein the electromagnetic field is generated by a Magnetic Resonance Imaging (MRI) scanner.

28. The method of claim 14, wherein the neurostimulation device is implanted within a patient.

* * * * *